United States Patent
Gupta et al.

(10) Patent No.: US 9,713,616 B2
(45) Date of Patent: Jul. 25, 2017

(54) PHARMACEUTICAL COMPOSITIONS COMPRISING L-LEUCOVORIN

(71) Applicant: Spectrum Pharmaceuticals, Inc., Irvine, CA (US)

(72) Inventors: Pramod Kumar Gupta, Rochester, NY (US); Bahman Shimiaei, Laguna Niguel, CA (US); Shaofeng Xie, Rancho Santa Margarita, CA (US)

(73) Assignee: Spectrum Pharmaceuticals, Inc., Henderson, NV (US)

( * ) Notice: Subject to any disclaimer, the term of this patent is extended or adjusted under 35 U.S.C. 154(b) by 0 days.

(21) Appl. No.: 14/419,904

(22) PCT Filed: Aug. 6, 2013

(86) PCT No.: PCT/US2013/053829
§ 371 (c)(1),
(2) Date: Feb. 5, 2015

(87) PCT Pub. No.: WO2014/025807
PCT Pub. Date: Feb. 13, 2014

(65) Prior Publication Data
US 2015/0164898 A1 Jun. 18, 2015

Related U.S. Application Data

(60) Provisional application No. 61/680,182, filed on Aug. 6, 2012.

(51) Int. Cl.
*A61K 31/519* (2006.01)
*A61K 9/00* (2006.01)
*A61K 47/02* (2006.01)
*A61K 31/513* (2006.01)

(52) U.S. Cl.
CPC .......... *A61K 31/519* (2013.01); *A61K 9/0019* (2013.01); *A61K 31/513* (2013.01); *A61K 47/02* (2013.01)

(58) Field of Classification Search
CPC .. A61K 31/519; A61K 31/513; A61K 9/0019; A61K 47/02; C07D 475/04
See application file for complete search history.

(56) References Cited

U.S. PATENT DOCUMENTS

| | | | |
|---|---|---|---|
| 4,931,441 A | 6/1990 | Lawrence | |
| 5,173,488 A * | 12/1992 | Haeger | A61K 9/0019 514/249 |
| 5,177,076 A | 1/1993 | Nijerk et al. | |
| 5,347,005 A | 9/1994 | Mueller et al. | |
| 5,814,635 A | 9/1998 | Buchs et al. | |
| 6,613,767 B1 | 9/2003 | Nijerk et al. | |
| 6,720,001 B2 | 4/2004 | Chen et al. | |
| 2006/0058312 A1 | 3/2006 | Miyagi et al. | |

FOREIGN PATENT DOCUMENTS

| WO | 2009/017624 A2 | 2/2009 |
|---|---|---|
| WO | 2014/025807 A1 | 2/2014 |

OTHER PUBLICATIONS

International Search Report and Written Opinion for International Application Serial No. PCT/US2013/053829 filed on Aug. 6, 2013.
Isovorin. EMC Medicine Guides. Provided by www.medicines.org.uk/guides. Last updated Sep. 13, 2011 (2010 Datapharm) (2 pages).
Kovoor et al., Is levoleucovorin an alternative to racemic leucovorin? A literature review. Clinical Colorectal Cancer, 8(4): 200-206 (2009).
Prescribing information for Fusilev® (levoleucovorin) revised Apr. 2011.

* cited by examiner

*Primary Examiner* — Sudhakar Katakam
(74) *Attorney, Agent, or Firm* — K&L Gates LLP; Louis C. Cullman; Robert W. Winn

(57) ABSTRACT

Compositions comprising a calcium salt of L-leucovorin may be prepared that have a higher concentration of L-leucovorin than may be prepared using racemic leucovorin under similar conditions. Thus, some pharmaceutical compositions described herein may comprise a calcium salt of L-leucovorin at a relatively high concentration, such as at least about 15 mg/mL. Such a composition may be a stable aqueous solution, and may have near physiological pH, such as about 6 to about 8. Some pharmaceutical compositions may be substantially free of D-leucovorin, and may contain either: a) no EDTA, or b) less than about 1 mg/ml of EDTA. These compositions may be prepared, for example, by sonicating a mixture comprising the solid calcium salt of L-leucovorin and water. In some compositions, a calcium salt of L-leucovorin may be sufficiently soluble that it does not precipitate when it is injected.

13 Claims, No Drawings

PHARMACEUTICAL COMPOSITIONS COMPRISING L-LEUCOVORIN

SUMMARY

Compositions comprising a calcium salt of L-leucovorin may be prepared that have a higher concentration of L-leucovorin than may be prepared using racemic leucovorin under similar conditions. Thus, some pharmaceutical compositions described herein may comprise a calcium salt of L-leucovorin at a relatively high concentration, such as at least about 15 mg/mL. Such a composition may be a stable aqueous solution, and may have near physiological pH, such as about 6 to about 8. Some pharmaceutical compositions may be substantially free of D-leucovorin, and may contain either: a) no EDTA, or b) less than about 1 mg/ml of EDTA. These compositions may be prepared, for example, by sonicating a mixture comprising the solid calcium salt of L-leucovorin and water. In some compositions, a calcium salt of L-leucovorin may be sufficiently soluble that it does not precipitate when it is injected.

Some embodiments include a pharmaceutical composition comprising a calcium salt of L-leucovorin at a concentration of at least about 15 mg/mL (referred to herein as "a pharmaceutical composition"), wherein the composition is a stable aqueous solution having a pH of about 6 to about 8, is substantially free of D-leucovorin, and contains either: a) no EDTA, or b) less than about 1 mg/mL of EDTA.

Some embodiments include a method of increasing the solubility of L-leucovorin, comprising: sonicating a mixture of L-leucovorin in an aqueous saline to increase the solubility of L-leucovorin; wherein the L-leucovorin is present in an amount of about 15 mg/mL to about 100 mg/mL; and wherein the L-leucovorin is sonicated until it is completely dissolved. Some embodiments include a solution of a calcium salt of L-leucovorin prepared by this or a related method. Some embodiments include a liquid dosage form comprising a solution of a calcium salt of L-leucovorin prepared by this or a related method.

Some embodiments include a liquid dosage form comprising a solution of a calcium salt of L-leucovorin prepared by a method comprising sonicating a mixture comprising L-leucovorin and water.

Some embodiments include a method of increasing the anti-cancer effects of a medication, comprising administering a pharmaceutical composition described herein to a mammal in need thereof.

Some embodiments include a method of treating a folic acid deficiency comprising administering a pharmaceutical composition described herein to a mammal in need thereof.

Some embodiments include a method of reducing a side effect of a medication, comprising administering a pharmaceutical composition described herein to a mammal in need thereof.

Some embodiments include a method of dissolving a calcium salt of L-leucovorin in saline comprising sonicating a mixture of a solid form of the calcium salt of L-leucovorin in saline until the calcium salt of L-leucovorin is completely dissolved in the saline solution. Some embodiments include a solution of a calcium salt of L-leucovorin prepared by this or a related method. Some embodiments include a liquid dosage form comprising a solution of a calcium salt of L-leucovorin prepared by this or a related method.

DETAILED DESCRIPTION

The chemical structure of a calcium salt of L-leucovorin is depicted below.

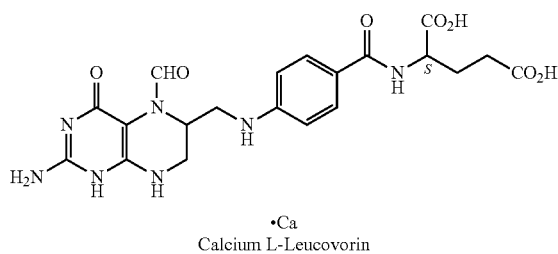

Calcium L-Leucovorin

Any suitable amount of a calcium salt of L-leucovorin that is at least about 15 mg/mL may be used in a pharmaceutical composition. For example, some pharmaceutical compositions may have a concentration of a calcium salt of L-leucovorin that is about 15 mg/mL to about 100 mg/mL, about 15 mg/mL to about 55 mg/mL, about 15 mg/mL to about 50 mg/mL, about 20 mg/mL to about 40 mg/mL, or about 25 mg/mL to about 45 mg/mL.

The pharmaceutical composition may be enriched in L-leucovorin, or may be substantially free of D-leucovorin. For example, the enantiomeric excess of L-leucovorin may be at least about 10%, at least about 50%, at least about 75%, at least about 90%, or at least about 95%.

A pharmaceutical composition may be free of EDTA or other complexing agents, or may contain low concentrations of EDTA or other complexing agents such that the compounds do not significantly complex calcium ions so as to significantly affect solubility of a calcium salt L-leucovorin. In some embodiments the amount of EDTA or another complexing agent may be about 4 mg/mL or less, about 2 mg/mL or less, about 1 mg/mL or less, or about 0.5 mg/mL or less, or a complexing agent may not be present.

A pharmaceutical composition can be a stable aqueous solution, including a solution that does not form solid precipitates over time. For example a stable aqueous solution could remain clear or free of precipitates for at least about 2 hours, at least about 15 hours, at least about 20 hours, at least about one week, at least about one month, at least about 6 months, or at least about one year. In some pharmaceutical compositions, the calcium salt of L-leucovorin has been dissolved in the pharmaceutical composition for at least about 2 hours, at least about 15 hours, at least about 20 hours, at least about one week, at least about one month, at least about 6 months, or at least about one year.

In some embodiments, a pharmaceutical composition may be free of any or all of the following compounds: ascorbic acid, sodium pyrosulfite, thioglycerol, cysteine hydrochloride, thioglycolic acid, sodium hydrogen sulfite, and/or sodium sulfite. In some embodiments a small amount of one of these compounds may be present, such as about 4 mg/mL or less, about 2 mg/mL or less, about 1 mg/mL or less, or about 0.5 mg/mL or less, An aqueous liquid pharmaceutical composition includes a liquid that is suitable for administration to a patient. An aqueous liquid pharmaceutical composition may be prepared using a physiological saline solution as a major vehicle. Pharmaceutical solutions may be maintained at a suitable pH, such as near physiological pH, with an appropriate buffer system, and may also contain other components, such as stabilizers, surfactants, etc.

A pharmaceutical composition may include a tonicity adjuster. The tonicity adjuster may vary, and may include any compound or substance useful for adjusting the tonicity of an ophthalmic liquid. Examples include, but are not limited to, salts, such as sodium chloride or potassium chloride, polyhydroxy compounds such as glycols, e.g. propylene glycol, sugars or sugar derivatives such as glucose, mannitol, or glycerin, etc., or any other suitable ophthalmically acceptable tonicity adjustor. The amount of tonicity adjuster may vary depending upon whether an isotonic, hypertonic, or hypotonic liquid is desired. In some embodiments, the amount of a tonicity agent such as those listed above may be at least about 0.0001% up to about 1%, about 2%, or about 5% (w/v). In some embodiments, a pharmaceutical composition may comprise sodium chloride at a concentration (w/v) of about 0.6% to about 1%, about 0.8% to about 0.9%, about 0.83%, or about 0.9%.

In some embodiments, the pharmaceutical composition may consist of, or consist essentially of a calcium salt of L-leucovorin and aqueous sodium chloride, such as aqueous sodium chloride at a concentration listed above. In some embodiments, a pharmaceutical composition may consist of, or consist essentially of a calcium salt of L-leucovorin; sodium chloride; hydrochloric acid, sodium hydroxide, or a combination thereof; and water. In some embodiments a pharmaceutical composition may consist of, or consist essentially of a calcium salt of L-leucovorin and water.

A pharmaceutical composition may include a buffer. The buffer may vary, and may include any weak conjugate acid-base pair suitable for maintaining a desirable pH range, such as about 6 to about 8, about 7 to about 8, about 7.2 to about 7.8, or about 7.4. Examples include, but are not limited to, acetate buffers, citrate buffers, phosphate buffers, borate buffers, lactate buffers, NaOH/Trolamine buffers, or a combination thereof such as phosphate and citrate or borate and citrate. Acids or bases, such as HCl and NaOH, may be used to adjust the pH of these formulations as needed. The amount of buffer used may vary. In some embodiments, the buffer may have a concentration in a range of about 1 nM to about 100 mM.

A pharmaceutical composition may include a surfactant. The surfactant may vary, and may include any compound that is surface active or can form micelles. A surfactant may be used for assisting in dissolving an excipient or an active agent, dispersing a solid or liquid in a composition, enhancing wetting, modifying drop size, stabilizing an emulsion, or a number of other purposes. Useful surfactants include, but are not limited to, surfactants of the following classes: alcohols; amine oxides; block polymers; carboxylated alcohol or alkylphenol ethoxylates; carboxylic acids/fatty acids; ethoxylated alcohols; ethoxylated alkylphenols; ethoxylated aryl phenols; ethoxylated fatty acids; ethoxylated; fatty esters or oils (animal & veg.); fatty esters; fatty acid methyl ester ethoxylates; glycerol esters; glycol esters; lanolin-based derivatives; lecithin and lecithin derivatives; lignin and lignin derivatives; methyl esters; monoglycerides and derivatives; polyethylene glycols; polymeric surfactants; propoxylated & ethoxylated fatty acids, alcohols, or alkyl phenols; protein-based surfactants; sarcosine derivatives; sorbitan derivatives; sucrose and glucose esters and derivatives. In some embodiments, the surfactant may include polyethylene glycol (15)-hydroxystearate (CAS Number 70142-34-6, available as Solutol HS 15® from BASF), polyoxyethylene-polyoxypropylene block copolymer (CAS No. 9003-11-6, available as Pluronic® F-68 from BASF), polyoxyethylene 40 stearate (POE40 stearate), polysorbate 80 or polyoxyethylene (80) sorbitan monooleate (CAS No. 9005-65-6), sorbitane monostearate (CAS No. 1338-41-6, available as Span™ 60 from Croda International PLC), or polyoxyethyleneglyceroltriricinoleate 35 (CAS No. 61791-12-6, available as Cremophor EL® from BASF), ethoxylated castor oil, such as Cremophor EL (CAS Number 61791-12-6). The amount of surfactant may vary. In some embodiments, the amount of any surfactant such as those listed above may be about 0.001 to about 5%, about 0.1% to about 2%, or about 0.1% to about 1%.

While there may be many ways to dissolve a calcium salt of L-leucovorin in water, one method includes sonicating a mixture of a solid form of a calcium salt of L-leucovorin in water until the calcium salt of L-leucovorin is completely dissolved in the water. Heating the mixture during sonication, for example to a temperature of at least about 30° C., at least about 40° C., or about 30° C. to about 100° C., about 40° C. about 90° C., about 40° C. to about 60° C., or about 40° C. to about 50° C., may help to dissolve the solid calcium salt. In some methods, sonication may be carried out for any suitable time such as at least about 15 min., at least about 30 min., at least about 45 min., at least about 60 min., at least about 1.5 hours, at least about 2 hours; up to about 2 hours, up to about 5 hours, up to about 10 hours, up to about 20 hours; or about 30 min. to about 10 hours, about 30 min. to about 5 hours, or for about 30 min. to about 2 hours.

A pharmaceutical composition may be used to treat a folic acid deficiency, reduce a side effect of a medication, such as a cancer medication, or increase anti-cancer effects of a medication, such as fluorouracil. For example, a pharmaceutical composition may be used for rescue after high-dose methotrexate therapy in osteosarcoma, diminishing the toxicity and counteracting the effects of impaired methotrexate elimination and of inadvertent overdosage of folic acid antagonists, and/or use in combination therapy with 5-fluorouracil in the palliative treatment of patients with advanced metastatic colorectal cancer. The term "treatment," "treat," or forms thereof, includes treatment, as well as diagnosis, cure, mitigation, or prevention of disease in man or other animals, or otherwise affecting the structure or any function of the body of man or other animals.

A pharmaceutical composition may be administered by any suitable means, such as injection, including intravenous injection. In some embodiments, a pharmaceutical composition may be administered by intravenous injection over a period of at least about 3 min., about 3 min. to about 30 min., or about 3 min. to about 15 min.

Any suitable dosage regime may be used. For example a pharmaceutical composition may be intravenously injected daily. In some embodiments, about 100 mg to about 500 mg, about 150 mg to about 300 mg, about 100 mg to about 500 mg, about 150 mg to about 250 mg, about 175 mg, or about 250 mg, of L-leucovorin may be administered in a single daily dose. A daily dose may be administered for about 1 day to about 30 days, about 3 days to about 10 days, or about 5 days. In some embodiments, an intravenous injection may be administered once daily for about 5 days, and may be repeated at 4-week intervals, for 2 courses and then repeated at 4 to 5-week intervals.

Example 1

L-leucovorin calcium (Merck) or racemic leucovorin calcium (Sigma) was added to water or aqueous sodium chloride (0.83%) and sonicated for about one hour. The mixtures were then stirred for about 20 hours at 5° C. The concentration of dissolved L-leucovorin calcium or racemic leucovorin calcium was determined at 15 min., 30 min., 1 hour, and 20 hours after sonication began. The results are reported in Table 1.

TABLE 1

| | Assay (mg/mL) | | | |
|---|---|---|---|---|
| | H₂O | | NaCl | |
| Time Pt. | L-Leu-covorin | Sigma Leucovorin Calcium | L-Leu-covorin | Sigma Leucovorin Calcium |
| 15 min. | 7.5 | 16.7 | 9.6 | 22.6 |
| 30 min. | 8.4 | 22.0 | 10.0 | 22.9 |
| 1 hr | 8.0 | 15.8 | 13.4 | 23.2 |
| 20 hrs | 11.9 | 3.3 | 17.4 | 7.4 |

Example 2

L-leucovorin calcium (Merck) or racemic leucovorin calcium (USP) was added to water or aqueous sodium chloride (0.83%) and sonicated at 40° C. to dissolve the L-leucovorin calcium or racemic leucovorin calcium. The solutions were then stirred at 5° C. for 20 hours. The concentration of dissolved L-leucovorin calcium or racemic leucovorin calcium was determined at 2 hours and 20 hours after stirring began. The results are reported in Table 2.

TABLE 2

| | Assay (mg/mL) | | | |
|---|---|---|---|---|
| | H₂O | | NaCl | |
| Time Pt. | L-Leu-covorin | USP Leucovorin Calcium | L-Leu-covorin | USP Leucovorin Calcium |
| 2 hrs | 31.9 | NA | 42.3 | NA |
| 20 hrs | 26.2 | 4.2 | 39.6 | 7.2 |

Example 3

L-leucovorin calcium (Merck) or racemic leucovorin (USP) calcium was added to water or aqueous sodium chloride (0.83%) and sonicated at 40° C. to dissolve the L-leucovorin calcium or racemic leucovorin calcium. The solutions were then stirred at 5° C. for 15 hours. At 2 hours, the solutions were purged with nitrogen gas and placed in a sealed vial. The concentration of dissolved L-leucovorin calcium or racemic leucovorin calcium was determined at two hours and 15 hours after sonication began. The results are reported in Table 3.

TABLE 3

| | Assay (mg/mL) | | | |
|---|---|---|---|---|
| | H₂O | | NaCl | |
| Time Pt. | L-Leu-covorin | USP Leucovorin Calcium | L-Leu-covorin | USP Leucovorin Calcium |
| 2 hrs | 40.4 | 3.6 | 49.2 | 8.4 |
| 15 hrs | 21.2 | 3.8 | 35.6 | 8.6 |

Example 4

L-leucovorin calcium (Merck) or racemic leucovorin calcium (Sigma) was added to water or aqueous sodium chloride (0.83%) and sonicated for 1 hour. The mixture was then stirred for an additional 19 hours 25° C. The concentration of dissolved L-leucovorin calcium or racemic leucovorin calcium was determined at 15 min., 30 min., 1 hour, or 20 hours after stirring began. The results are reported in Table 4.

TABLE 4

| | Assay (mg/mL) | | | |
|---|---|---|---|---|
| | H₂O | | NaCl | |
| Time Pt. | L-Leu-covorin | Sigma Leucovorin Calcium | L-Leu-covorin | Sigma Leucovorin Calcium |
| 15 min. | 14.9 | 52.9 | 20.2 | 42.1 |
| 30 min. | 15.1 | 53.3 | 20.4 | 41.9 |
| 1 hr | 16.1 | 50.1 | 21.6 | 39.6 |
| 20 hrs | 23.6 | 9.0 | 32.4 | 14.2 |

Example 5

L-leucovorin calcium (Merck) or racemic leucovorin calcium (USP) was added to water or aqueous sodium chloride (0.83%) and sonicated at 40° C. for about half an hour. The mixture was then stirred at 25° C. for 20 hours. The concentration of dissolved L-leucovorin calcium or racemic leucovorin calcium was determined at two hours and 20 hours. The results are reported in Table 5.

TABLE 5

| | Assay (mg/mL) | | | |
|---|---|---|---|---|
| | H₂O | | NaCl | |
| Time Pt. | L-Leu-covorin | USP Leucovorin Calcium | L-Leu-covorin | USP Leucovorin Calcium |
| 2 hrs | 31.9 | NA | 42.3 | NA |
| 20 hrs | 31.1 | 13.4 | 42.1 | 17.4 |

Example 6

L-leucovorin calcium (Merck) or racemic leucovorin (USP) calcium was added to water or aqueous sodium chloride (0.83%) and sonicated at 40° C. for one hour to dissolve the L-leucovorin calcium or racemic leucovorin calcium. The solutions were then stirred at 25° C. for an additional hour. After 2 hours, the solutions were purged with nitrogen and placed in a sealed vial. The mixtures were then stirred for an additional 18 hours. The concentration of dissolved L-leucovorin calcium or racemic leucovorin calcium was determined at two hours and 20 hours after sonication began. The results are reported in Table 6.

TABLE 6

| | Assay (mg/mL) | | | |
|---|---|---|---|---|
| | H₂O | | NaCl | |
| Time Pt. | L-Leu-covorin | USP Leucovorin Calcium | L-Leu-covorin | USP Leucovorin Calcium |
| 2 hrs | 40.4 | 10.1 | 49.2 | 16.1 |
| 20 hrs | 42.3 | 10.8 | 53.1 | 17.1 |

Unless otherwise indicated, all numbers expressing quantities of ingredients, properties such as molecular weight, reaction conditions, and so forth used in the specification and claims are to be understood as being modified in all instances by the term "about." Accordingly, unless indicated to the contrary, the numerical parameters set forth in the specification and attached claims are approximations that may vary depending upon the desired properties sought to be obtained. At the very least, and not as an attempt to limit the application of the doctrine of equivalents to the scope of the claims, each numerical parameter should at least be construed in light of the number of reported significant digits and by applying ordinary rounding techniques.

The terms "a," "an," "the" and similar referents used in the context of describing the invention (especially in the context of the following claims) are to be construed to cover both the singular and the plural, unless otherwise indicated herein or clearly contradicted by context. All methods described herein can be performed in any suitable order unless otherwise indicated herein or otherwise clearly contradicted by context. The use of any and all examples, or exemplary language (e.g., "such as") provided herein is intended merely to better illuminate the invention and does not pose a limitation on the scope of any claim. No language in the specification should be construed as indicating any non-claimed element essential to the practice of the invention.

Groupings of alternative elements or embodiments disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Certain embodiments are described herein, including the best mode known to the inventors for carrying out the invention. Of course, variations on these described embodiments will become apparent to those of ordinary skill in the art upon reading the foregoing description. The inventor expects skilled artisans to employ such variations as appropriate, and the inventors intend for the invention to be practiced otherwise than specifically described herein. Accordingly, the claims include all modifications and equivalents of the subject matter recited in the claims as permitted by applicable law. Moreover, any combination of the above-described elements in all possible variations thereof is contemplated unless otherwise indicated herein or otherwise clearly contradicted by context.

In closing, it is to be understood that the embodiments disclosed herein are illustrative of the principles of the claims. Other modifications that may be employed are within the scope of the claims. Thus, by way of example, but not of limitation, alternative embodiments may be utilized in accordance with the teachings herein. Accordingly, the claims are not limited to embodiments precisely as shown and described.

The invention claimed is:

1. A pharmaceutical composition comprising a calcium salt of L-leucovorin at a concentration greater than about 20 mg/mL, wherein the composition is a stable aqueous solution having a pH of about 6 to about 8, is substantially free of D-leucovorin, and contains either: a) no EDTA, or b) less than about 1 mg/mL of EDTA; and wherein the aqueous solution remains free of precipitates for at least about 20 hours.

2. The pharmaceutical composition of claim 1, having a pH of about 7.2 to about 7.8.

3. The pharmaceutical composition of claim 1, which is substantially free of calcium complexing agents.

4. The pharmaceutical composition of claim 1, wherein the concentration of the calcium salt of L-leucovorin is about 25 mg/mL to about 50 mg/mL.

5. The pharmaceutical composition of claim 1, further comprising sodium chloride.

6. The pharmaceutical composition of claim 1, consisting essentially of a calcium salt of L-leucovorin, and water or aqueous sodium chloride.

7. The pharmaceutical composition of claim 1, consisting essentially of a calcium salt of L-leucovorin; sodium chloride; hydrochloric acid, sodium hydroxide, or a combination thereof; and water.

8. The pharmaceutical composition of claim 1, wherein the calcium salt of L-leucovorin is sufficiently soluble that it does not precipitate on storage.

9. The pharmaceutical composition of claim 1, wherein the calcium salt of L-leucovorin has been dissolved in the composition for at least 2 hours.

10. The pharmaceutical composition of claim 1, wherein the calcium salt of L-leucovorin has been dissolved in the composition for at least 20 hours.

11. A method of dissolving a calcium salt of L-leucovorin in water to obtain the pharmaceutical composition of claim 1, the method comprising sonicating a mixture of a solid form of the calcium salt of L-leucovorin in saline until the calcium salt of L-leucovorin is completely dissolved in the saline.

12. The method of claim 11, wherein the mixture is sonicated for at least about 30 minutes.

13. The method of claim 11, wherein the mixture is sonicated at a temperature of at least about 40° C.

* * * * *